United States Patent [19]

Sawyer et al.

[11] Patent Number: 4,468,297

[45] Date of Patent: Aug. 28, 1984

[54] DEGRADATION AND DETOXIFICATION OF HALOGENATED OLEFINIC HYDROCARBONS

[75] Inventors: Donald T. Sawyer; Thomas S. Calderwood, both of Riverside, Calif.

[73] Assignee: Regents of the University of California, Berkeley, Calif.

[21] Appl. No.: 469,873

[22] Filed: Feb. 25, 1983

[51] Int. Cl.$^3$ .............................................. C25B 3/02
[52] U.S. Cl. ................................. 204/59 R; 423/419 R; 423/500
[58] Field of Search ................. 204/59 R; 423/419 R, 423/500

[56] References Cited

U.S. PATENT DOCUMENTS 3,677,916  7/1972  Seiber et al. ...................... 204/59 R

OTHER PUBLICATIONS

"The Chemistry of Superoxide Ion", Sawyer, D. T. & Gibian, M. J.; *Tetrahedron*, vol. 35, 1979, pp. 1471–1481.
"Electrochemical Studies of the Reactivity of Superoxide Ion With Several Alkyl Halides in Dimethyl Sulfoxide", Merritt, M. V., Sawyer, D. T.; *Journ. of Organic Chemistry*, 35, 1970, pp. 2157–2159.
"Nucleophilic Reactions of Electrogenerated Superoxide Ion", Dietz, R.; Forno, A. E. J.; Larcombe, B. E. & Peover, M. E.; *Journ. Chem. Soc.*, B, 1970, pp. 816–820.
Dietz et al., Chemical Abstracts vol. 72, Abstract 85626t (1970).
Fleischmann et al., Chemical Abstracts, vol. 70, Abstract 56925t (1969).
"The Reaction of Superoxide with Alkyl Halides and Tosylates", Chern, C-I.; San Filippo, Jr., J.; Valentine, J. S.; *J. Org. Chem.*, vol. 40, No. 11, 1975, pp. 1678–1680.
"Superoxide Chemistry. A Convenient Synthesis of Dialkyl Peroxides"; Johnson, R. A.; Nidy, E. G.; *J. Org. Chem.*, vol. 40, No. 11, 1975, pp. 1680–1681.
"Cleavage of Esters by Superoxide"; Chern, C-I.; San Filippo, Jr., J.; Romano, L. J.; *J. Org. Chem.*, vol. 41, No. 3, 1976, pp. 586–588.
"On the Reaction Kinetics of Electrogenerated Superoxide Ion with Aryl Benzoates"; Bontempelli, G.; Magno, F.; *J. Electroanal. Chem.*, 68, 1976, pp. 337–344.
"Reactivity of Superoxide Ion with Carbonyl Compounds in Aprotic Solvents"; Gibian, M. J.; Morrison, M. M.; Sawyer, D. T.; Tangpoonpholvivat, R.; Ungermann, T.; *J. American Chem. Soc.*, 101:3, 1979, pp. 640–644.
"A Study of the Reaction Kinetics of Electrogenerated Superoxide Ion with Benzylbromide"; Magno, F.; Seeber, R.; Valcher, S.; *J. Electroanal. Chem.*, 83, 1977, pp. 131–138.
"Nucleophilic Reactions of Superoxide Anion Radical"; Arudi, R. L.; Danen, W. C.; Warner, R. J.; *Organic Free Radicals, ACS Symposium Series* 69; Prior, W. A., ed.; 1978, pp. 244–257.
"The Electrochemical Reduction of Superoxide Ion and Oxidation of Hydroxide Ion in Dimethyl Sulfoxide"; Goolsby, A. D.; Sawyer, D. T.; *Analytical Chemistry*, vol. 40, No. 1, 1968, pp. 83–86.
*Advanced Organic Chemistry;* March, J.; 2nd ed.; McGraw-Hill, N.Y., 1977, pp. 342–343.
"Mechanisms of protection against the damage produced in biological systems by oxygen-derived radicals"; Slater, T. F.; *Oxygen Free Radicals and Tissue Damage; Ciba Foundation Symposium* 65; Elsevier/North-Holland: N.Y., 1979, pp. 143–163.
*Experimental Electrochemistry for Chemists;* Sawyer, D. T.; Robert, J. L., Jr.; John Wiley & Sons, New York, 1974, pp. 167–215 (Chapter Four).
"Chemical and Physical Properties of Superoxide", Fee, J. A. and Valentine, J. S.; *Superoxide and Superoxide Dismutases,* Academic Press, 1977, pp. 19, 53, 58.
Allen, *Organic Electrode Processes,* pp. 90, 91, pub. by Chapman & Hall Ltd., London (1958).
Rifi et al., *Introduction to Org. Electrochem,* pp. 214, 215, pub. by Marcel Dekker, Inc., N.Y. (1974).
Fry et al., "Electrolyte Effects upon the Polarographic Reduction of Alkyl Halides in Dimethyl Sulfoxide", *J. Org. Chem.*, vol. 41, No. 1, pp. 54–57 (1976).
"How Super is Superoxide?", Sawyer, D. T. et al., *Acc. Chem. Res.* 14, pp. 393–400 (1981).
LeBerre, A.; Berguer, Y., *Bull. Soc. Chem. Fr.,* pp. 2363–2374 (1966).
Schmidt, M.; Bipp, H., *Z. Anorg. Ally. Chem.,* 303, pp. 190–200 (1960).
"The Reaction of Superoxide Anion Radical With Electron Poor Olefins", Frimer et al., *Tetrahedron Letters,* No. 52, pp. 4631–4634 (1977).
"Facile Degradation of Superoxide Ion of Carbon Tetrachloride, Chloroform, Methylene Chloride, and p,p'-DDT in Aprotic Media", Roberts et al., *J. Am. Chem. Soc.*, 103, pp. 712–714 (1981).

*Primary Examiner*—John F. Niebling
*Attorney, Agent, or Firm*—Nilsson, Robbins, Dalgarn, Berliner, Carson & Wurst

[57] ABSTRACT

Halogenated olefinic hydrocarbons that contain at least two halogen atoms are degraded by reaction in an aprotic solvent with a strong nucleophile selected from the superoxide ion and hydroxide ion to give oxygenated products and inorganic chloride ion. In specific embodiments, superoxide ion is electrolytically generated in dimethylformamide that contains a soluble electrolyte and multi-halogenated olefins such as 1,1-dichloro ethylene, cis-1,2-dichloroethylene, trichloroethylene and tetrachloroethylene, which are degraded. In addition, various substituted derivatives of such compounds react in a similar manner to give related oxygenated products.

14 Claims, No Drawings

DEGRADATION AND DETOXIFICATION OF HALOGENATED OLEFINIC HYDROCARBONS

ACKNOWLEDGEMENT

The government has rights in this invention pursuant to Grant No. CHE-79-22040 awarded by the National Science Foundation.

FIELD OF THE INVENTION

The invention pertains to the fields of oxidation processes and electrolytic material treatment.

BACKGROUND AND SUMMARY OF THE INVENTION

Halogenated compounds contribute significantly to the problem of disposing of chemical wastes, as such compounds are often toxic and presently must be either shipped hundreds of miles from shore to be incinerated or stored in dumps for toxic wastes. In the past, negligence in locating such dumps has had catastrophic consequences in exposing large populations to the adverse health effects of toxic compounds. As a result, massive cleanup efforts are presently being undertaken to degrade and detoxify these compounds. Pesticides are a particular problem in this regard, as virtually all of such compounds are toxic to man to a greater or lesser degree, and some are particularly resistant to biodegradation. For example, olefinic pesticides such as dichlorodiphenyldichloroethylene has been particularly difficult to degrade, as have other halogenated olefinic hydrocarbon wastes from industrial sources.

There is thus a clear need for an efficient and safe method to degrade toxic halogenated olefins to harmless and environmentally compatible products. However, such a method has heretofore been elusive. Although primary and secondary alkylhalides are readily oxidized by superoxide ion in aprotic media via a bimolecular nucleophilic substitution ($S_N2$) mechanism; (M. V. Merritt; D. T. Sawyer, *J. Org. Chem.*, 35 (1970) p. 2157; R. Dietz; A. E. J. Forno; B. E. Lancombe; M. E. Peover, *J. Chem. Soc. B* (1970), p. 816; J. San Fillipo, Jr.; C. -I. Chern; J. S. Valentine, *J. Org. Chem.*, 40 (1975) p. 1678; R. A. Johnson; E. G. Nidy, *J. Org. Chem.*, 40 (1975) p. 1680; simple olefins are unreactive (A. Leberre; Y. Berguer, *Bull. Soc. Chem. Fr.* (1966) p. 2363; M. Schmidt; H. Bipp, *Z. Anorg. Ally. Chem.*, 303 (1960) p. 190; A. Frimer; I. Rosenthal; S. Hoz, *Tetrahedron Ltt.*, 52 (1977) p. 4631. In addition, in a recent study of polychloro hydrocarbons, it has been observed that chloroethylene and trichloroethylene do not react at significant rates with superoxide in dimethyl sulfoxide (J. L. Roberts, Jr.; D. T. Sawyer, *J. Am. Chem. Soc.;* 103 (1981) p. 712. One aspect of the problem relates to the wide diversity of such compounds, ranging from such simple molecules as carbon tetrachloride and chloroform to complex insecticides such as p-p'-dichlorodiphenyltrichloroethane (p-p'-DDT). A related aspect of the problem relates to the theoretical consideration that as one increases the number of halogen atoms covalently joined to a tetrahedral carbon atom, one should experience a striking decrease in reactivity of the halogen atoms as a result of increasing steric hindrance to inversion of the tetrahedral configuration (as well as the neighboring orbital overlap attributable to electron repulsion between the incoming nucleophile and the multiple halogens. This is consistent with a mechanism involving bimolecular nucleophilic substitution ($S_N2$) (see J. San Fillipo, Jr.; C. -I. Chern; J. S. Valentine; "The Reaction of Superoxide with Alkyl Halides and Tosylates," *J. Org. Chem.*, 40 (1975) p. 1678 and R. A. Johnson; E. G. Nidy,"Superoxide Chemistry—A Convenient Synthesis of Dialkyl Peroxides," *J. Org. Chem.*, 50 (1975) p. 1680 and presents an even greater problem with regard to olefinic hydrocarbons due to the rigidity of the alkene bond.

Additional information regarding the degradation of halogenated carbon compounds and the problems of steric hindrance associated therewith is contained in U.S. patent application Ser. No. 221,077 filed Dec. 29, 1980, U.S. Pat. No. 4,410,402 which is hereby incorporated by reference.

Thus, there is a clear need for an efficient, safe means to degrade the multi-halogenated olefinic hydrocarbons that are wastes from solvent industries, dry cleaning establishments and the machine and foundry industries. The limitations on the reactivity of multi-halogenated olefinic hydrocarbons accentuate the formidable nature of the problem.

In accordance with the present invention, a process is provided which overcomes the foregoing problems and in particular is one which appears to fly in the face of such limitations. Specifically, we have discovered that a strong nucleophile such as the superoxide or hydroxide ion reacts rapidly and efficiently with multi-halogenated olefinic hydrocarbons and pesticides in aprotic solvents to give oxygenated products and inorganic chloride ions. For example, we have discovered that the conversion of 1,1-dichloroethylene to carbonate ions and formaldehyde in an electrolyte system of tetramethylammonium chloride in dimethylformamide proceeds at a surpising rate. The cathode for the system can be constructed from platinum, graphite, glassy carbon, or mercury. The cathode compartment of the cell is saturated at one atmosphere with either air or molecular oxygen. The anode can be constructed from similar materials and can either contain the electrolyte when cadmium or mercury is used for the electrode, or, for other electrode materials, a depolarizer such as hydrazine may be added to the compartment.

We have also found that an efficient method for converting olefinic halides is to conduct the foregoing reaction in a controlled-potential electrolysis cell, wherein the superoxide ion is electrolytically generated in an aprotic solvent with electrolyte. While it is known that superoxide ion can be generated electrolytically for reaction with alkyl halides in an aprotic solvent such as dimethylsulfoxide (e.g. Merritt, et al., supra), because of the constraints outlined above, such a process has not heretofore been used for the degradation or detoxification of multi-halogenated olefinic wastes of the type effectively treated in accordance with the present invention.

More particularly, multi-halogenated olefinic hydrocarbon wastes are introduced into an electrolysis cell that contains an aprotic solvent (with electrolyte), such as dimethylformamide. With the cathode compartment saturated with air or oxygen, the cathode potential is set at about $-1.0$ V vs saturated calomel electrode (SCE) to generate $\rightarrow O_2^-$. The resultant $\rightarrow O_2^-$ reacts with the multi-halogenated olefinic hydrocarbons as described. As the degradation process progresses, the solution will become saturated with the reaction products which will then precipitate out as solids. Such a system consumes less than 60 Kcal of electrical energy per mol of olefinic halogen degraded.

DETAILED DESCRIPTION OF THE PREFERRED EMBODIMENT

Reaction with the superoxide ion or hydroxide ion must take place in an aprotic solvent. Such solvents are well known; see D. T. Sawyer; J. L. Roberts, Jr., *Experimental Electrochemistry for Chemists*, John Wiley & Sons, New York, pp. 167-215 (1974) (Chapter Four). Aprotic solvents generally have hydrogen bound only to carbon and are at best poor hydrogen-bond donors; they are weakly acidic and proton exchange occurs slowly. Useful aprotic solvents include those which do not form powerful hydrogen bonds with water, such as various amides, nitriles, ethers and other materials; specific examples include pyridine, acetonitrile (MeCN), benzonitrile, dimethylformamide (DMF), N-methyl-2-pyrrolidone, propylene carbonate, sulfolane, and hexamethylphosphoramide.

In accordance with a preferred embodiment, the polyhalogenated olefinic compounds are reacted with superoxide ion in an electrolytic system which generates the superoxide ion in an aprotic solvent with electrolyte. The resultant superoxide reacts with the polyhalogenated olefinic compounds that are present in the solvent system to form oxygenated products. As electrolyte, one can use any of a variety of organic solvent soluble electrolytes, for example, tetraethylammonium perchlorate, tetra-n-butyl-ammonium perchlorate, tetraethylammonium boron tetrafluoride, tetra-n-butyl ammonium boron tetrafluoride, tetraethylammonium bromide, tetramethylammonium chloride and tetra-n-butyl ammonium bromide.

In the general form of the invention, as an alternative approach, chemically synthesized superoxide or hydroxide, for example, in the form of tetramethylammonium superoxide or tetraethylammonium hydroxide, can be used in an aprotic solvent in place of the electrolytic system; or the superoxide can be in the form of $KO_2$, which can be solubilized in dimethyl sulfoxide with the aid of dicyclohexyl-18-crown-6. Such solubilization is reported by Johnson et al., supra. One could also use a soluble hydroxide in aprotic solvent, for example, tetraethylammonium hydroxide, tetra-n-butylammonium hydroxide, or tetra-n-propylammonium hydroxide, which may be added in alcohol, e.g. methanol to the aprotic solvent.

The extent of the reaction of electrogenerated $O_2^-$ with multichloro olefins was determined by cyclic voltammetry of $O_2$ in the presence of excess substrate. The overall reaction and product stoichiometries for the degradation of the multichloro substrated by $O_2^-$ in DMF are summaried in Table 1.

Stoichiometries were determined by incremental titration with substrate of a known amount of $O_2^-$ (~4 mM, electrosythesized), with the residual $O_2$ determined by positive-scan voltammetry. The $O_2$ from the stroichiometric combination of substrate and $O_2^-$ in a sealed cell was determined by cyclic voltammetry. The yield of $Cl^-$ was determined by anodic cyclic voltammetry at $+0.95$ V vs SCE (confirmed by $AgNO_3$ titration), and the yield of base (after dilution with $H_2O$) by titration with HCl (titration curves for the product solutions were identical to that for bicarbonate ion).

The rates of reaction for the respective substrates with $O_2^-$ have been measured by the rotating ring-disc voltammetric technique. A Pine Instruments Co. Model RPE 3 dual potentiostat in combination with a Pt-Pt ring-disc electrode was used for the kinetic studies. Oxygen was reduced at the disc to $O_2^-$, which travelled to the ring where it was oxidized to $O_2$. The ratio of currents, i(ring)/i(disc) decreased when a reactive substrate (with $O_2^-$) was present in excess. Pseudo first-order rate constants were determined for the $O_2^-$-substrate reactions with a ten-fold excess by use of analytical functions (W. J. Albery; M. L. Hitchman, "Ring-Disc Electrodes," Clarendon Press, Oxford (1971). These constants exhibit a first-order dependence on substrate concentration. The normalized pseudo first-order rate constants ($k_1/[S]$) are summarized in Table 1. Essentially, the same apparent rate constants and reaction stoichiometries are observed when MeCN is used as the solvent, but in Me2SO the apparent rate constants, $k_1/[S]$, are 10-100 times smaller.

Within the limits of a reaction time of ten minutes or less, 1-chloroethylene, trans-1,2-dichloroethylene, Aldrin, and Dieldrin are not oxidized by $O_2^-$ in DMF.

The lack of significant reactivity between $O_2^-$ and $CH_2=CHCl$, trans-$CHCl=CHCl$, Aldrin and Dieldrin indicates that the facile oxidation of cis-$CHCl=CHCl$ must involve an unhindered nucleophilic addition of $O_2^-$ to one of the carbon centers. A reasonable possibility is nucleophilic displacement of a chloride ion with the formation of a dioxetane activated complex, with subsequent addition of another $O_2^-$ to give an intermediate acid-chloride and bicarbonate ion.

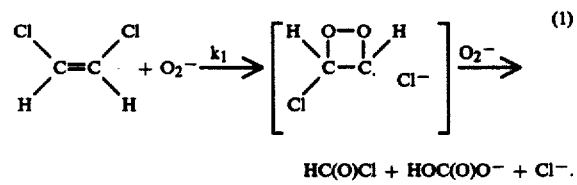

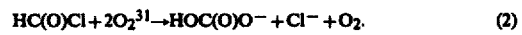

$HC(O)Cl + HOC(O)O^- + Cl^-$.

The acid-chloride reacts with two more $O_2^-$ ions:

$$HC(O)Cl + 2O_2^{3-} \rightarrow HOC(O)O^- + Cl^- + O_2. \quad (2)$$

The reaction of $CH_2=CCl_2$ with $O_2^-$, which is slower than for the cis isomer, must involve a similar nucleophilic addition. The dioxetane activated complex apparently adds a second $O_2^-$:

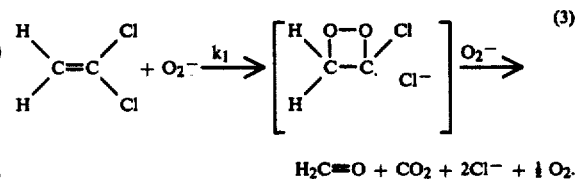

$H_2C=O + CO_2 + 2Cl^- + \frac{1}{2} O_2$.

The $CO_2$ reacts with another $O_2^-$ ion plus residual water

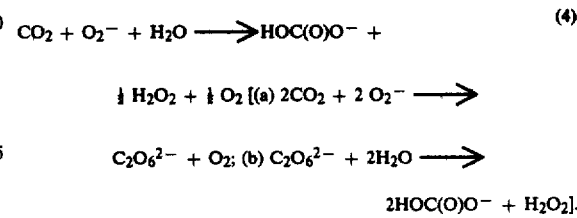

We have confirmed that substituted derivatives of these four examples react in a similar manner to give related oxygenated products; that is, the hydrogen of the three exemplary multi-halogenated olefins can be replaced with alkyl or aryl substituents without altering the overall degradation processes. Thus, the pesticide DDE (a derivative of DDT) is converted to a much less toxic substance and one that is water soluble

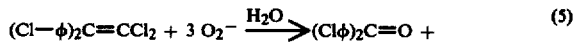 (5)

$$2Cl^- + HOC(O)O^- + \tfrac{1}{2} H_2O_2 + O_2.$$

 (6)

A preferable embodiment of this process chemistry involves the use of dimethylformamide (DMF) (0.1 M tetraethylammonium perchlorate). Other solvents such as dimethyl sulfoxide (DMSO) and pyridine work equally well for the processes indicated by the above reactions. We believe the degradation chemistry for the examples is general for most multi-halogenated olefinic hydrocarbons. However, the trans isomer of 1,2-dichloroethylene only reacts at an extremely slow rate.

The reactivity of the dehydrohalogenation product of DDT [(ClPh)$_2$C=CCl$_2$(DDE)] with $O_2^-$ is identical to that for CH$_2$=CCl$_2$ in terms of stoichiometry, apparent rate constant, and products.

The mechanisms for the oxygenation by $O_2^-$ of CHCl=CCl$_2$ and Cl$_2$C=CCl$_2$ probably involve a combination of those for cis-CHCl=CHCl and for H$_2$C=CCl$_2$. The rates of reaction increase as the number of chlorine atoms increase; the yield of dioxygen also increases to three O$_2$ molecules for the six $O_2^-$ ions that react with tetrachloroethylene. Thus, the net electroreductive activation of O$_2$ for reaction with CCl$_2$=CCl$_2$ can be represented by

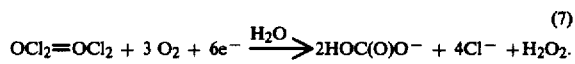 (7)

With sufficiently slow voltage scans the height of the O$_2$ reduction peak (in the presence of excess CCl$_2$=CCl$_2$) is enhanced by a factor of two.

The proposed dioxetane intermediates of equations 1 and 3 may be produced in biological matrices by the in vivo generation and reaction of $O_2^-$ with ingested chloroethylenes. These and other radical intermediates from the $O_2^-$ substrate reaction are likely toxins and their reactivity with lipids may represent the mechanism for the cyto-toxicity of cleaning solvents in the liver.

The aprotic solvents dimethylformamide and acetonitrile are thus seen to provide a degradation of multi-halogenated olefinic hydrocarbons which is particularly advantageous with regard to the reaction rate of the degradation. In similar experiments, pyridine has provided a similar reaction. While not wishing to be bound by any particular theory, it is now thought that DMSO fails to react at significant rates due to the singular proclivity of DMSO to form a powerful hydrogen-bonded complex with water and the fact that trace amounts of water are very difficult to remove from DMSO. Thus, as DMSO is substantially more water-like than other aprotic solvents, this deactivating effect is apparently crucial with regard to the to the degradation of multi-halogenated olefinic hydrocarbons. However, if the water-bonding tendency of DMSO may be overcome or limited by methods presently or hereinafter known in the art, this aprotic solvent may be used without departing from the spirit of the invention.

Although the foregoing invention has been described in some detail by way of illustration and example, changes in form and the substitution of equivalents are contemplated as circumstances may suggest or render expedient; and although specific terms have been employed herein, they are intended in a descriptive sense and not for purposes of limitation, the scope of the invention being delineated in the claims.

TABLE 1

| Reactions of Superoxide ion with multichloroethylenes in dimethylformamide | | | | | |
|---|---|---|---|---|---|
| Substrate (S) 1–10 M | $O_2^-$ per S | $Cl^-$ released per S | $HOC(O)O^-$ released per S | $O_2$ released per S | $k_1/[S]$, $M^{-1}s^{-1}$ |
| cis-CHCl=CHCl | 4 | 2 | 2 | 0 | 10 |
| CH$_2$=CCl$_2$ | 3 | 2 | 1 | 1 | 2 |
| CHCl=CCl$_2$ | 5 | 3 | 2 | 1.5 | 9 |
| CCl$_2$=CCl$_2$ | 6 | 4 | 2 | 3 | 15 |
| (p-ClPh)$_2$C=CCl$_2$ (DDE) | 3 | 2 | 1 | 1 | 2 |

Overall reactions:

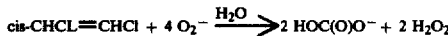

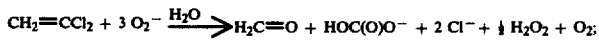

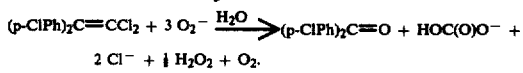

$$2 Cl^- + \tfrac{1}{2} H_2O_2 + O_2.$$

We claim:

1. A process for the degradation of a hydrocarbon compound containing an olefinic bond and at least two halogen atoms selected from chlorine, bromine and iodine on the carbon atoms adjacent the olefinic bond, comprising reacting said hydrocarbon compound with a strong nucleophile selected superoxide and hydroxide in an aprotic solvent which is essentially free of water to form oxygenated hydrocarbon products and inorganic halogen ions.

2. The process of claim 1 in which said nucleophile is superoxide ion.

3. The process of claim 2 in which said superoxide ion is electrolytically generated in an electrolytic cell fitted with an anode and a cathode and containing said aprotic solvent adjacent said cathode, said aprotic solvent containing an electrolyte soluble therein.

4. The process of claim 3 including the step of introducing the hydrocarbon compound into the aprotic solvent adjacent the cathode and generating superoxide ion at the cathode to react with the hydrocarbon compound.

5. The process of claim 4 in which the hydrocarbon compound is introduced in a solvent therefor.

6. The process of claim 1 in which the nucleophile is hydroxide ion.

7. The process of claim 1 wherein at least two of the halogen atoms on the carbon atoms adjacent the olefinic bond are in a cis relationship.

8. The process of claim 7 in which said nucleophile is superoxide ion.

9. The process of claim 2 in which the aprotic solvent is dimethylformamide or acetonitrile.

10. The process of claim 7 in which the aprotic solvent is dimethylformamide or acetonitrile.

11. The process of claim 2 wherein the hydrocarbon compound is selected from the group consisting of 1,1-dichloroethylene; cis-1,2-dichloroethylene; trichloroethylene; tetrachloroethylene and dichlorodiphenyldichloroethylene.

12. The process of claim 7 wherein the hydrocarbon compound is selected from the group consisting of 1,1-dichloroethylene; cis-1,2-dichloroethylene; trichloroethylene; tetrachloroethylene and dichlorodiphenyldichloroethylene.

13. The process of claim 9 wherein the hydrocarbon compound is selected from the group consisting of 1,1-dichloroethylene; cis-1,2-dichloroethylene; trichloroethylene; tetrachloroethylene and dichlorodiphenyldichloroethylene.

14. A process for the electrolytic degradation of a hydrocarbon compound selected from the group consisting of 1,1-dichloroethylene; cis-1,2-dichloroethylene; trichloroethylene; tetrachloroethylene and dichlorodiphenyldichloroethylene, said process comprising:

providing an electrolytic cell fitted with an anode and a cathode and containing an aprotic solvent selected from the group consisting of dimethylformamide or acetonitrile adjacent the cathode, the aprotic solvent containing an electrolyte soluble therein and being substantially free of water;

adding the hydrocarbon compound to said aprotic solvent;

electrolytically generating superoxide ion at the cathode to react with the hydrocarbon compound to form a degradation product thereof, the degradation product reacting with the aprotic solvent to form chloride ion and bicarbonate; and removing said chloride ion and bicarbonate from the electrolytic cell.

* * * * *